US006611703B2

United States Patent
Kuth et al.

(10) Patent No.: US 6,611,703 B2
(45) Date of Patent: Aug. 26, 2003

(54) APPARATUS FOR EXAMINING CONTRAST AGENT MOVEMENTS UNDER THE EFFECT OF GRAVITY

(76) Inventors: Rainer Kuth, Herzogenaurach (DE); Thomas Rupprecht, Uttenreuth (DE)

( * ) Notice: Subject to any disclaimer, the term of this patent is extended or adjusted under 35 U.S.C. 154(b) by 112 days.

(21) Appl. No.: 09/770,008

(22) Filed: Jan. 25, 2001

(65) Prior Publication Data

US 2001/0012914 A1 Aug. 9, 2001

(30) Foreign Application Priority Data

Jan. 28, 2000 (DE) .......................... 100 03 726

(51) Int. Cl.$^7$ ................................................ A61B 5/05
(52) U.S. Cl. .................................................. 600/415
(58) Field of Search .............................. 600/415, 410, 600/407; 324/318, 322; 5/681

(56) References Cited

U.S. PATENT DOCUMENTS

| 5,694,935 A | * | 12/1997 | Damadian ................ 5/601 |
| 5,724,970 A | * | 3/1998 | Votruba et al. ........... 5/601 |
| 5,807,255 A | * | 9/1998 | Yokota et al. ............ 5/601 |
| 5,810,729 A | * | 9/1998 | Hushek et al. ........... 324/307 |
| 5,931,781 A | * | 8/1999 | De Boer ................. 324/318 |
| 5,991,651 A | * | 11/1999 | LaBarbera ............... 5/601 |
| 6,134,464 A | * | 10/2000 | Tan et al. ............... 324/309 |
| 6,195,578 B1 | | 2/2001 | Distler et al. |
| 6,216,294 B1 | * | 4/2001 | Wess ..................... 5/615 |
| 6,230,040 B1 | * | 5/2001 | Wang et al. ............. 324/309 |
| 6,311,085 B1 | * | 10/2001 | Meaney et al. ........... 324/306 |

* cited by examiner

Primary Examiner—Teresa Walberg
Assistant Examiner—Daniel Robinson

(57) ABSTRACT

An apparatus for examining contrast agent movement in the body of a patient under the effect of gravity has an MR scanner with a patient support system which can be tilted around the longitudinal axis and/or transverse center axis for placing the patient in an oblique position within the magnet.

8 Claims, 1 Drawing Sheet

APPARATUS FOR EXAMINING CONTRAST AGENT MOVEMENTS UNDER THE EFFECT OF GRAVITY

BACKGROUND OF THE INVENTION

1. Field of the Invention

The present invention relates to an apparatus for examining contrast agent movements in the body of a patient under the effect of gravity.

2. Description of the Prior Art

In radiography procedures, the flow of a contrast agent through the body under the effect of gravity has for many years been examined to provide certain diagnostic information. It is of particular importance in the case of the organs of digestion and the kidney/bladder system. Radiography procedures, however, are always associated with exposure to ionizing radiation, all the more so when the time pattern of a flow is to be monitored by means of a large number of images. Radiography contrast agents are physiologically harmful and in some cases slightly toxic.

SUMMARY OF THE INVENTION

An object of the invention is to provide an apparatus for examining contrast agent movements in the body of a patient under the influence of gravity which avoids radiation exposure, particularly in children and adolescents, and additionally provides enhanced soft tissue contrast, by which means the diagnostic precision can be improved. In addition, water is to be used as the contrast agent.

This object is achieved according to the invention in an apparatus having an MR scanner with a patient support system which can be tilted around the longitudinal axis and/or the transverse center axis for placing the patient in an oblique position within the magnet.

Minimally invasive interventions have in recent years already been performed increasingly with MR image control, these interventions being restricted by the confined space within the magnet, particularly in a complex and long apparatus. Despite this, it has not been proposed to examine the flow of contrast agent in the body under the effect of gravity using a magnetic resonance scanner, even though the required basic technologies are available, as well as the desire to spare patients, and in particular children, from radiation exposure. However, extensive tests forming the basis of the present invention have shown that even a relatively slightly inclined position, as is possible especially in the modem and no longer quite so confined MR scanners, particularly in open systems, permits a flow of contrast agent, under the effect of gravity, which is adequate for diagnostic examination. In addition to the possibility of simply providing an inclined wedge for corresponding oblique positioning of the patient on a normal support plate (as a result of which much of the restricted space in the MR scanner is nevertheless lost), a first embodiment of a patient support apparatus according to the invention has a lifting and pivoting column which is arranged next to the MR scanner and supports a patient support plate on a cantilevered bearing arm.

By means of this lifting and pivoting column support, not only can a patient support be tilted around its longitudinal axis, i.e. the patient being tilted around his or her body axis, but also the support can be inclined so that the head is higher than the patient's feet, and in this way the typical gravitational flow of the contrast agent can take place. In this arrangement, the drive mechanism is advantageously installed in the base, where the magnetic stray field of the MR magnet is small. All movable parts are made of non-magnetic material, for example aluminum or V4A stainless steel. The holding apparatus for the patient is made of a high-strength material which is additionally compatible with the electromagnetic conditions in the MR scanner, i.e. it is nonmagnetic and nonconductive, and has a small tan δ and an extremely short echo time. Examples of suitable materials for this purpose are glass-fiber-reinforced plastic or Kevlar-reinforced plastic.

German Utility Model 299 005 12 discloses a magnetic resonance apparatus with a patient support table which can be used as an operating table, with patient support table mounted on the operating column so that it can be tilted around an axis transverse to the longitudinal axis of the table. However, in this known arrangement, with a column alongside the patient support table, tilting is only possible outside the magnet, and this is deliberately the case. The tilting in this known apparatus is in fact intended to facilitate certain operations. Examination of the patient within the magnet, especially with contrast agent flow, is not provided for at all.

Instead of a pivoting arrangement with a lateral lifting and pivoting column, in a further preferred embodiment of the invention provides the patient support system has a support shell which can be tilted, preferably in two directions perpendicular to each other, and the support shell can be mounted in a floating manner on an air cushion in a second support shell.

This patient support system with a tiltable support shell makes it possible, even in confined systems, to tilt the patient in order to obtain a flow of contrast agent under the effect of gravity, which is practically impossible when tilting the entire support arm with the patient support plate around a transverse axis on a lifting and pivoting column.

DESCRIPTION OF THE PREFERRED EMBODIMENTS

Figure 1:
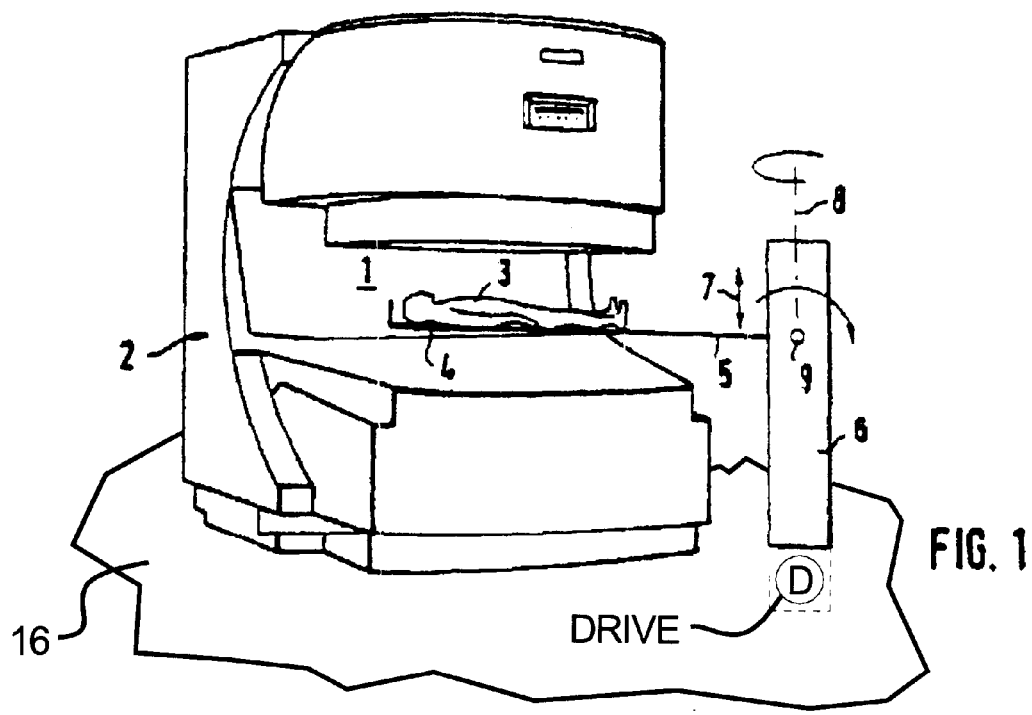
FIG. 1 shows a diagrammatic view of an MR scanner with a lateral lifting and pivoting column for a pivotable and tiltable patient support constructed and operating in accordance with the invention.

In the examination space 1 of the open MR scanner 2 in the illustrative embodiment shown in FIG. 1, a patient 3 is arranged on a patient support 4 which is connected via a supporting arm 5 to a lifting and pivoting column 6. The lifting column 6 is arranged next to the MR scanner 2 and permits a multiplicity of different lifting and pivoting movements of the patient support 4. In addition to a vertical displacement indicated by the double arrow 7, the support 4 can be pivoted around the vertical axis 8 of the lifting and pivoting column 6 by means of the supporting arm 5 and thus can be swung from a loading and unloading position outside the MR scanner 2 into the examination position within the examination space 1 of the MR scanner 2. In addition, the supporting arm 5 with the patient support 4 can be pivoted around a horizontal axis 9, resulting in an oblique position of the patient's body in which the head is higher than the feet, or vice versa, in order to achieve a flow of contrast agent through the body under the effect of gravity, which can be examined with the aid of the MR scanner, without the previously necessary high radiation exposure.

In the illustrative embodiment, use is made of a commercially available MR scanner (SIEMENS Magnetom OPEN) from which the usual patient table has been removed. The free space, in particular the height of the examination space 1, is sufficient to achieve an adequate oblique position of the patient 3 (this applies especially to children, for whom such examinations are needed particularly often). In this position contrast agent flows through the body under the effect of gravity and thus permits examination.

The MR scanner 2 is disposed on a floor sixteen, and a drive D for effecting the above-described movements of the supporting arm 5 can be disposed in a base of the column 6 below the level of the floor 16.

Instead of the arrangement of the patient support system shown in FIG. 1, patient support can be obtained with a tiltable support shell 10 which stands on prop wedges 11 and accordingly permits a slight pivoting in the direction of the double arrow 12, in order to modify the horizontal orientation of the head and feet of the patient 3 relative to the horizontal position shown.

Figure 2:
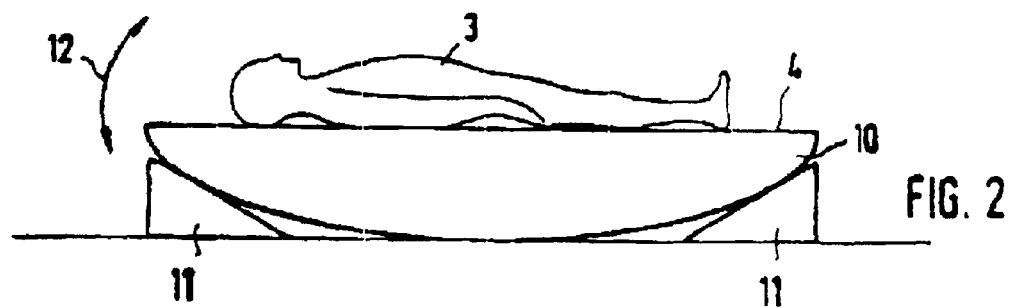
FIG. 2 shows a side view of an embodiment of a patient support system with a tiltable support shell, constructed and operating in accordance with the invention.
Figure 3:
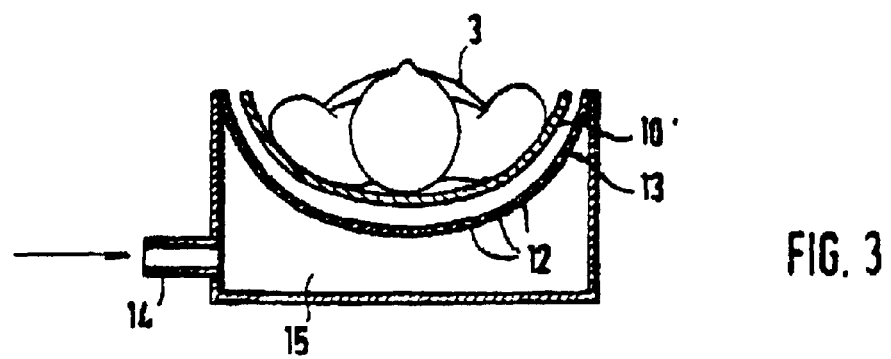
FIG. 3 shows a cross section through a support shell arrangement with air cushion constructed and operating in accordance with the invention.

FIG. 3 shows a particularly advantageous variant of such a support shell arrangement according to FIG. 2, where the patient 3 lies in the support shell 10' and not, as in FIG. 2, on a patient support 4 arranged on the latter. The support shell 10' is enclosed by a second support shell 13 containing a multiplicity of air passages 12, so that air, introduced via an air admission pipe 14 into a chamber 15 below the second support shell 13, passes between the two support shells 10' and 13 and an air cushion can build up therebetween, on which air cushion the support shell 10' supporting the patient can be pivoted in a manner practically free from friction. The pivoting can in this case take place around the patient's longitudinal axis and also around a transverse axis, as is shown in FIG. 2. Compared to the mechanically mounted support shell shown in FIG. 2, the semicircular arrangement according to FIG. 3 also has the advantage that rotation around the center point or center axis of the patient is possible, thus avoiding shifting from the measurement volume upon movements of the patient.

The invention is not limited to the illustrative embodiments shown. In addition to other possible configurations of a tiltable support system, or at least one permitting an oblique position of the patient, the invention can be used with tubular MR scanners, in other words not just with open systems as in FIG. 1, since even the modem closed systems have substantially greater diameters than previously, thus permitting an oblique position affording an adequate flow of contrast agent, especially in the case of infant patients.

The MR measurement could in this case be carried out as sequence measurement with the so-called True Fisp procedure with a high layer thickness. This affords kinematic studies of the contrast agent movement. True Fisp provides section images in very short time and tolerates curvatures of the organ to be examined within the measurement section.

In the case of dubious structures, it is also possible to switch to small layer thicknesses and high resolution, with correspondingly extended measurement time.

Arranging the MR image monitor on the magnet permits interactive contrast agent control in real time.

Although modifications and changes may be suggested by those skilled in the art, it is the intention of the inventors to embody within the patent warranted hereon all changes and modifications as reasonably and properly come within the scope of their contribution to the art.

We claim:

1. A magnetic resonance examination apparatus comprising:

a magnetic resonance scanner having an imaging volume; and a patient support system having a patient support shell adapted to receive a patient thereon containing contrast agent, said patient support element having a longitudinal axis and a transverse center axis, and said patient support system including a tilting apparatus connected to said patient support element for selectively tilting said patient support element around said longitudinal axis and said transverse center axis for orienting an entirety of a patient on said patient support element in an oblique position relative to either or both of said longitudinal axis and said transverse center axis, with at least a portion of said patient within said imaging volume, for producing contrast agent movement within said patient due to gravity.

2. An apparatus as claimed in claim 1 wherein said magnetic resonance scanner is an open magnetic resonance scanner.

3. An apparatus as claimed in claim 1 wherein said tilting arrangement is a lifting and pivoting column disposed next to said magnetic resonance scanner having a cantilevered supporting arm connected to said patient support element.

4. An apparatus as claimed in claim 3 wherein said lifting and pivoting column has a base, and further comprising a drive unit for operating said lifting and pivoting column disposed in said base.

5. An apparatus as claimed in claim 4 wherein said base is disposed below floor level.

6. An apparatus as claimed in claim 1 wherein said support shell is a first support shell, and wherein said patient support system further comprises a second support shell, and a pressurized air system for producing an air cushion between said first support shell and said second support shell so that said first support shell floats on said air cushion above said second support shell.

7. An apparatus as claimed in claim 1 further comprising a magnetic resonance monitor mounted on said magnetic resonance scanner.

8. A method for conducting a magnetic resonance examination of a subject, comprising the steps of:

providing a magnetic resonance scanner having an imaging volume;

injecting contrast agent into a patient;

placing at least a portion of said patient, with said contrast agent therein, in said imaging volume on a patient support element having a longitudinal axis and a transverse center axis; and operating said magnetic resonance scanner with a True Fisp imaging sequence, while tilting said patient support element around either or both of said longitudinal axis and said transverse center axis for orienting an entirety of said patient on said patient support element obliquely relative to either or both of said longitudinal axis and said center transverse axis with at least a portion of said patient in said imaging volume to examine contrast agent movement in said patient due to gravity.

* * * * *